United States Patent [19]

Tsuchiya et al.

[11] Patent Number: 5,672,514
[45] Date of Patent: Sep. 30, 1997

[54] CHEMILUMINESCENT DETECTING METHOD AND APPARATUS

[75] Inventors: Tohru Tsuchiya; Taizo Akimoto, both of Kanagawa-ken; Keiji Mori, Tokyo; Yasushi Kojima, Kanagawa-ken, all of Japan; Günter Dietzel, Straubenhardt, Germany; Gerhard Petz, Essen, Germany; Andreas Köpke, Scheden, Germany

[73] Assignee: Fuji Photo Film Co., Ltd., Kanagawa, Japan

[21] Appl. No.: 588,854

[22] Filed: Jan. 19, 1996

[30] Foreign Application Priority Data

| Feb. 1, 1995 | [JP] | Japan | 7-015153 |
| Mar. 10, 1995 | [JP] | Japan | 7-051465 |
| Mar. 17, 1995 | [JP] | Japan | 7-059198 |

[51] Int. Cl.⁶ .............. G01N 33/48; G01N 21/76; G01N 23/04
[52] U.S. Cl. .............. 436/86; 430/56; 430/94; 430/172; 430/501; 422/52; 435/6; 250/484.4; 250/581; 250/582; 250/583; 250/584; 250/585; 250/586
[58] Field of Search ............... 250/581–586, 250/484.4; 422/52; 435/6; 436/56, 94, 172, 501, 86

[56] References Cited

U.S. PATENT DOCUMENTS

| 4,239,968 | 12/1980 | Kotera et al. | 250/327.1 |
| 4,539,137 | 9/1985 | Kohda et al. | 252/301.4 H |
| 4,640,898 | 2/1987 | Halfman | 436/546 |
| 4,865,967 | 9/1989 | Shiraishi et al. | 435/6 |
| 4,962,047 | 10/1990 | Place | 436/518 |
| 5,013,916 | 5/1991 | Umemoto et al. | 250/327.2 |
| 5,260,190 | 11/1993 | Shiraishi et al. | 435/6 |
| 5,270,162 | 12/1993 | Shiraishi et al. | 435/6 |

FOREIGN PATENT DOCUMENTS

| 58-69281 | 4/1983 | Japan . |
| 59-56479 | 3/1984 | Japan . |
| 1-60782 | 12/1989 | Japan . |
| 1-60784 | 12/1989 | Japan . |
| 2-276997 | 11/1990 | Japan . |
| 4-3952 | 1/1992 | Japan . |
| 4-232864 | 8/1992 | Japan . |
| 2246197 | 1/1992 | United Kingdom . |
| WO 9313405 | 7/1993 | WIPO . |
| WO 9421821 | 9/1994 | WIPO . |

OTHER PUBLICATIONS

Y. Amemiya et al. *Nature* 1988, 336, 89–90.
R. F. Johnston et al. *Electrophoresis* 1990, 11, 355–360.
O. Nishikawa et al. *Applied Surf. Sci.* 1994, 76/77, 359–366.
Q. Nguyen et al. *Anal. Biochem.* 1995, 226, 59–67.

*Primary Examiner*—Arlen Soderquist
*Attorney, Agent, or Firm*—Sughrue, Mion, Zinn, Macpeak and Seas

[57] ABSTRACT

A chemiluminescent detecting method includes the steps of uniformly irradiating with radiation a stimulable phosphor sheet formed with a stimulable phosphor layer containing a stimulable phosphor which can store an energy of radiation and be stimulated by visible light to emit the energy of radiation in a form of light, thereby storing energy of radiation uniformly therein, selectively labeling a biopolymer with a labeling substance which can produce chemiluminescent light by contact of itself and a chemiluminescent substance, causing the biopolymer labeled with the labeling substance and the chemiluminescent substance to come into contact with each other, and exposing the stimulable phosphor sheet to chemiluminescent light produced by the contact of the biopolymer labeled with the labeling substance and the chemiluminescent substance. According to this chemiluminescent detecting method, it is possible to effectively produce information relating to a biopolymer such as information relating to a gene with high accuracy by using a stimulable phosphor sheet which can be easily handled and used for both the chemiluminescent detecting method and the autoradiographic detecting method.

15 Claims, 9 Drawing Sheets

FIG. 3A
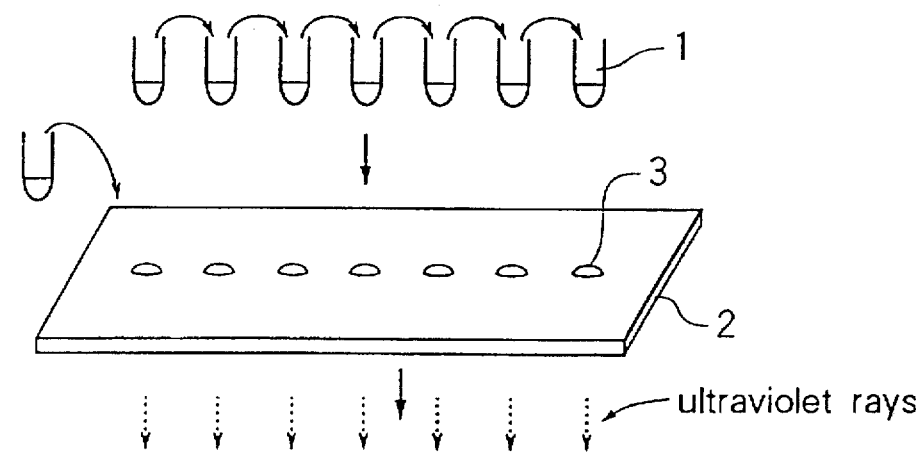
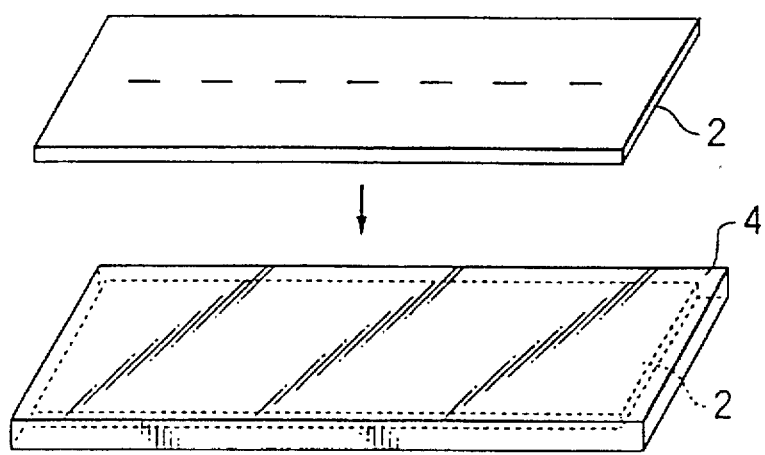
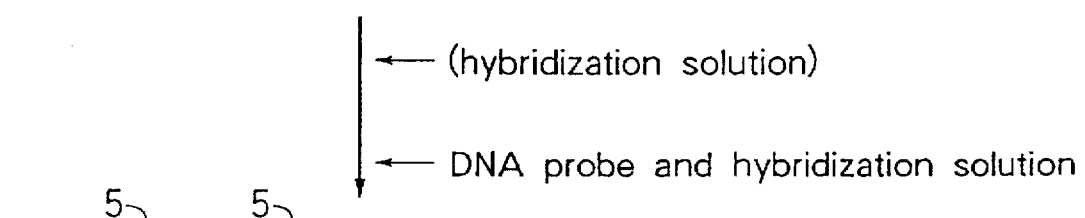
← (hybridization solution)
← DNA probe and hybridization solution
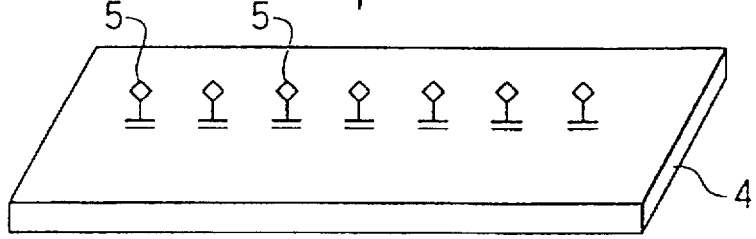
← alkaline phosphatase solution
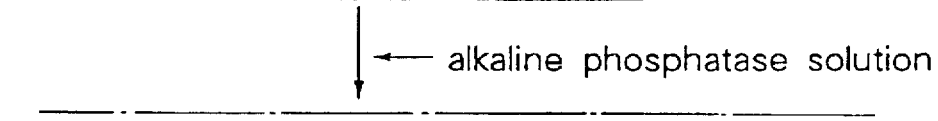
FIG. 3B

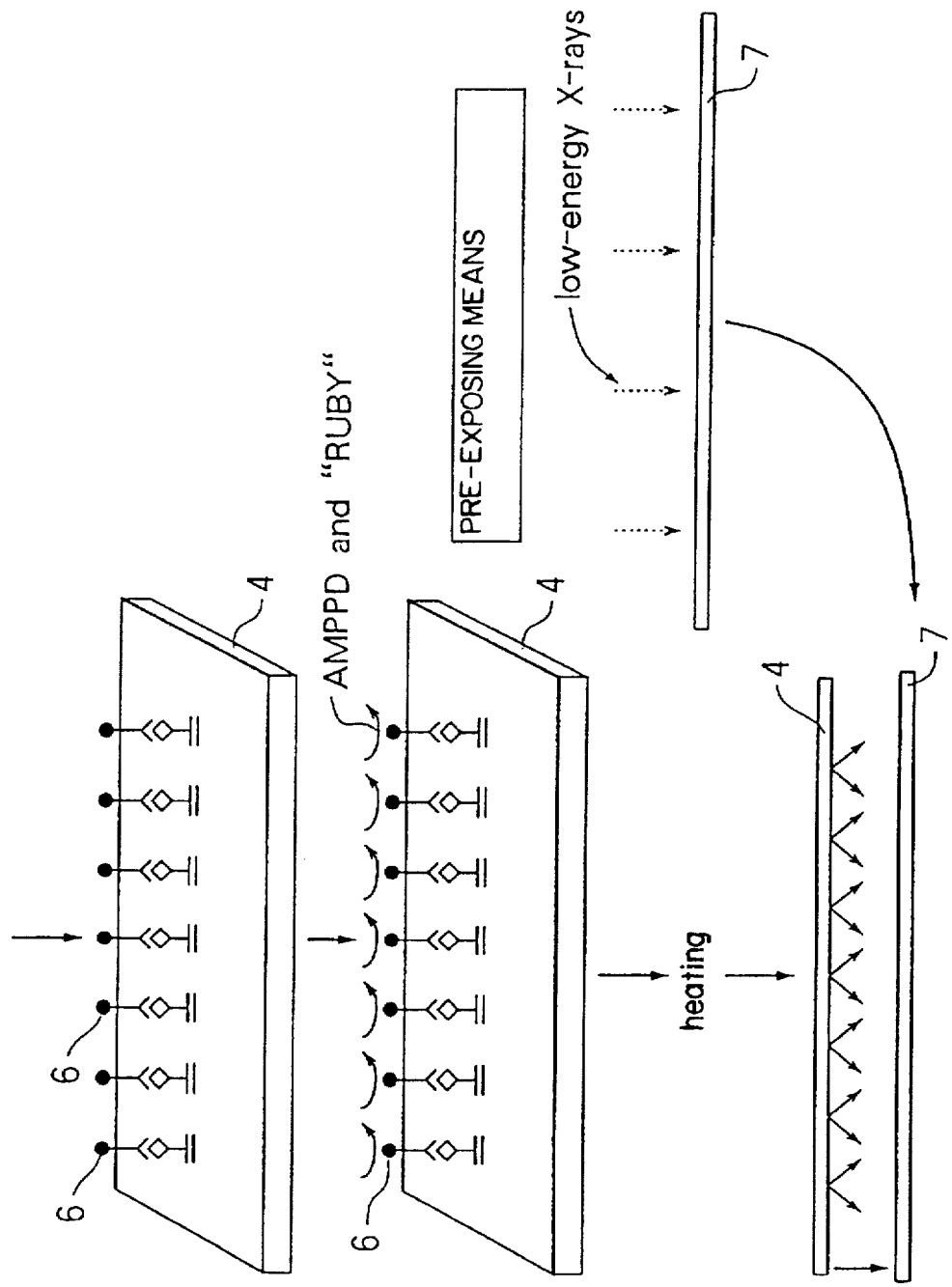

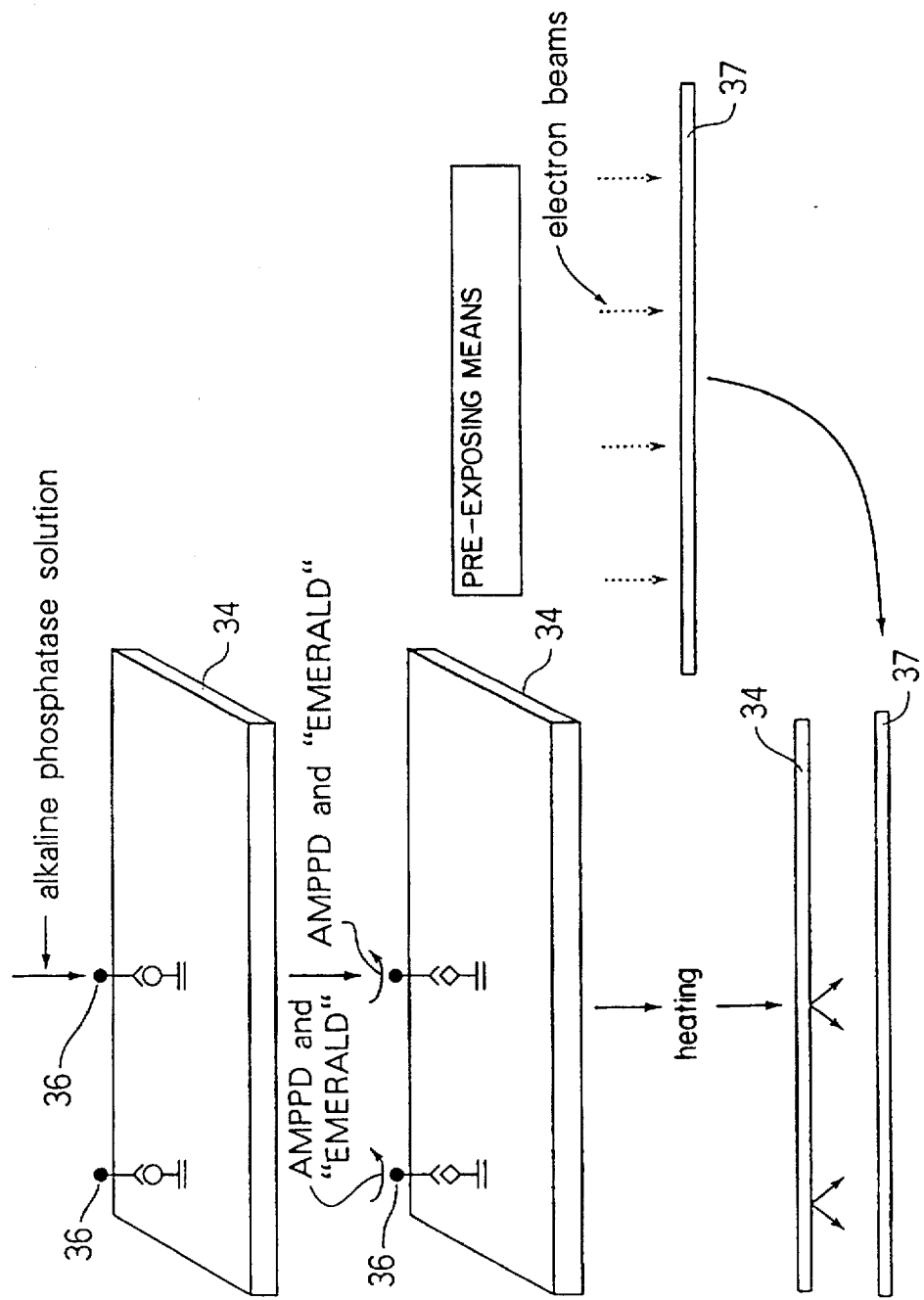

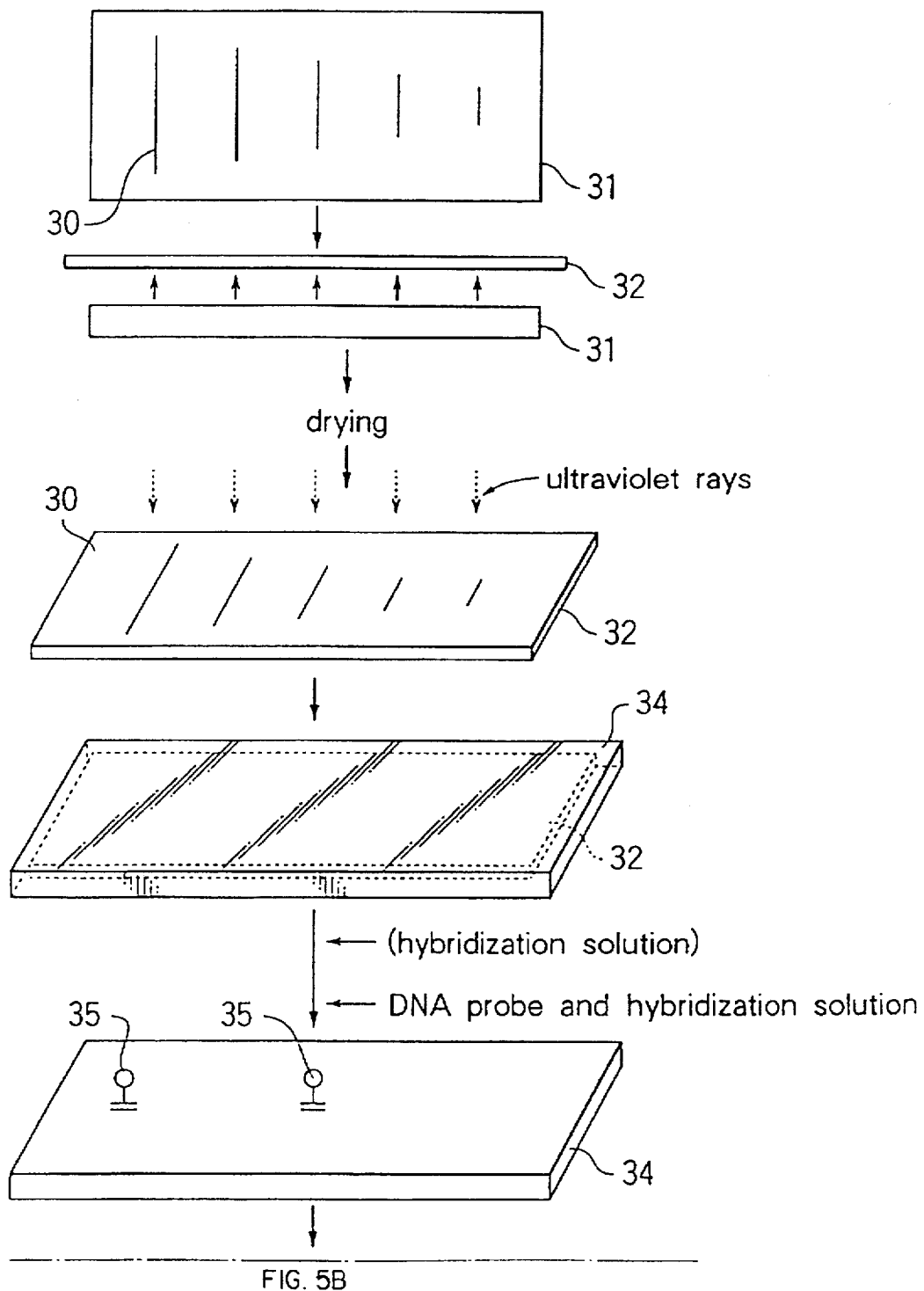

CHEMILUMINESCENT DETECTING METHOD AND APPARATUS

BACKGROUND OF THE INVENTION

The present invention relates to a chemiluminescent detecting method and apparatus for producing locational information relating to a labeling substance in a biopolymer, and, particularly, to such a method and an apparatus using stimulable phosphors.

DESCRIPTION OF THE PRIOR ART

There is known a chemiluminescent process comprising the steps of selectively labeling a fixed biopolymer such as a protein or a nucleic acid sequence with a labeling substance which generates chemiluminescent emission when it contacts a chemiluminescent substance, contacting the biopolymer selectively labeled with the labeling substance and the chemiluminescent substance, detecting the chemiluminescent emission in the wavelength of visible light generated by the contact of the chemiluminescent substance and the labeling substance and obtaining information relating to the biopolymer such as genetic information.

The chemiluminescent detecting process is widely used for determining the base sequence of DNA, RNA or the like obtained by electrophoresis, screening genes obtained by electrophoresis or colony hybridization, producing reference data regarding genes obtained by dot-blotting, the simple detection of gene amount and expression amount, the separation or identification of a protein and the estimation of the molecular weight or properties of a protein or the like.

Conventionally, the detection of chemiluminescence is effected by exposing a photographic film to chemiluminescent emission emitted from a biopolymer and developing it, thereby detecting a visible image. However, this method has a major drawback. Although the very weak chemiluminescent emission produced by the contact of the chemiluminescent substance and the labeling substance makes it necessary to employ a highly sensitive photographic film having a high gamma value for reliably detecting the chemiluminescent emission, when a highly sensitive photographic film having a high gamma value is employed, it is difficult to expose the film reliably using a straight portion of the characteristic curve. Therefore, the film is often exposed improperly and it is necessary to repeatedly expose photographic films of different sensitivity or under various exposure conditions. Further, it is indispensable to chemically develop the films and, therefore, the operations are unavoidably complicated. Furthermore, since in the case where an image produced by the exposure of a photographic film is analyzed by the eyes, it is difficult to detect information relating to a biopolymer such as information relating to a gene with high accuracy, it is further necessary to scan the image produced by the exposure of a photographic film with light, convert the visible image to digital signals, signal-process them and analyze them, and, therefore, the operations are unavoidably complicated.

There is also known a chemiluminescent detecting method comprising the steps of employing a stimulable phosphor sheet formed with a stimulable phosphor layer containing a stimulable phosphor which can store the energy of visible light upon being irradiated therewith, be stimulated upon being irradiated with an electromagnetic wave such as visible light, ultraviolet rays, infrared rays or the like to emit light the amount of which is proportional to the energy of the visible light stored therein, storing and recording chemiluminescent emission produced by the contact of the chemiluminescent substance and the labeling substance, scanning the stimulable phosphor sheet with an electromagnetic wave such as visible light, ultraviolet rays, infrared rays or the like to cause it to emit the energy of the chemiluminescent emission stored and recorded therein, converting the emitted light to digital signals, effecting image processing on the obtained digital signals and producing information relating to a biopolymer such as information relating to a gene (For example, Japanese Patent Application Laid Open No. 4-232864 and the like).

According to this chemiluminescent detecting method using the stimulable phosphor sheet, since when irradiated with an electromagnetic wave, the stimulable phosphor emits light whose amount is proportional to the energy of visible light with which it was irradiated, improper exposure becomes rare as compared with the use of a photographic film, while development, which is a chemical processing, becomes unnecessary. Therefore, the operations become simple. In addition, since information relating to a biopolymer such as information relating to a gene can be obtained in the form of digital signals, it is possible to analyze information relating to a biopolymer such as information relating to a gene with high accuracy by effecting necessary image processing on the digital signals. Use of a stimulable phosphor in this process is therefore advantageous.

However, in this chemiluminescent detecting method, since the stimulable phosphor stores the energy of visible light when irradiated therewith, it is necessary to shield it from visible light and, therefore, the handling of the stimulable phosphor sheet is troublesome.

On the other hand, there is known for the same purpose as that of the chemiluminescent detecting method, an autoradiographic detecting method for producing locational information relating to a radioactively labeled substance in medium containing tissue of an organism and/or substances derived from an organism with a radioactively labeled substance by labeling the tissue and/or substances derived from the organism with a radioactively labeled substance. Moreover, there has been proposed an autographic detecting method using, as a detecting material for producing locational information relating to a radioactively labeled substance, a stimulable phosphor sheet formed with a stimulable phosphor layer containing a stimulable phosphor which can store the energy of radiation and release stimulated emission whose amount is proportional to the energy of the radiation with which the stimulable phosphor sheet was irradiated upon being irradiated with an electromagnetic wave such as visible light, infrared rays or the like (For example, Japanese Patent Publication No. 1-60784, Japanese Patent Publication No. 1-60782, Japanese Patent Publication No. 4-3952 and the like).

Since this autoradiographic detecting method is used for the same purpose as the chemiluminescent detecting method, it is preferable for users to be able to select, based on the specimen concerned, between the autoradiographic detecting method and the chemiluminescent detecting method for obtaining information relating to high molecular substances such as information relating to genes.

However, since it is necessary to detect visible light generated by the contact of the chemiluminescent substance and the labeling substance in the chemiluminescent detecting method, whereas it is necessary to detect radiation in the autoradiographic detecting method, the same kind of stimulable phosphor sheet cannot be used for both methods.

SUMMARY OF THE INVENTION

It is therefore an object of the present invention to provide a chemiluminescent detecting method and apparatus which can effectively produce information relating to a biopolymer such as information relating to genes with high accuracy by using a stimulable phosphor sheet which can be easily handled and used for both a chemiluminescent detecting method and an autoradiographic detecting method.

The above and other objects of the present invention can be accomplished by a chemiluminescent detecting method comprising steps of uniformly irradiating with radiation a stimulable phosphor sheet formed with a stimulable phosphor layer containing a stimulable phosphor, which can store an energy of radiation and be stimulated by visible light to emit the energy of radiation in a form of light, thereby storing energy of radiation uniformly therein, selectively labeling a biopolymer with a labeling substance which can produce chemiluminescent light by contact of itself and a chemiluminescent substance, causing the biopolymer labeled with the labeling substance and the chemiluminescent substance to come into contact with each other, and exposing the stimulable phosphor sheet to chemiluminescent light produced by the contact of the biopolymer labeled with the labeling substance and the chemiluminescent substance.

The above and other objects of the present invention can be also accomplished by a chemiluminescent detecting apparatus comprising an accommodating member capable of transmitting visible light, for accommodating a biopolymer selectively labeled with a labeling substance which can produce chemiluminescent light by contact between itself and a chemiluminescent substance, pre-exposing means for uniformly irradiating with radiation a stimulable phosphor sheet formed with a stimulable phosphor layer, containing a stimulable phosphor which can store energy of radiation and be stimulated by visible light to emit the energy of radiation in a form of light, thereby obtaining a pre-exposed stimulable phosphor sheet which stores energy of radiation uniformly therein, stimulating light irradiating means, for irradiating with stimulating light the pre-exposed stimulable phosphor sheet after it has released energy of radiation stored therein in the form of light owing to exposure to chemiluminescent light produced by contact of the labeling substance and the chemiluminescent substance, and detecting means for photoelectrically detecting light emitted from the stimulable phosphor sheet upon irradiation with the stimulating light.

In a preferred aspect of the present invention, the chemiluminescent substance contains a sensitizing agent which can change the wavelength of light emitted from the chemiluminescent substance.

In a further preferred aspect of the present invention, the stimulable phosphor is a barium fluorohalide phosphor and the sensitizing agent contains poly-[vinylbenzyl (benzyl dimethyl ammonium chloride)] shown by the following general formula as a main component.

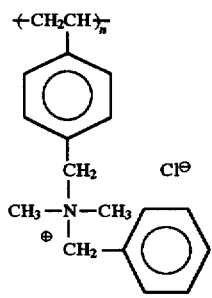

(1)

In a further preferred aspect of the present invention, the sensitizing agent contains a very small amount of fluorescent dye and a surface active agent.

In a further preferred aspect of the present invention, the radiation includes X-rays, α-rays, β-rays, γ-rays and electron beams.

In a further preferred aspect of the present invention, X-rays having an energy equal to or less than 20 KV are selected as the radiation.

In a further preferred aspect of the present invention, electron beams having an energy equal to or less than 100 KV are selected as the radiation.

In a further preferred aspect of the present invention, the stimulable phosphor sheet which has been exposed to the chemiluminescent light is scanned with an electromagnetic wave to be stimulated and light emitted from the stimulable phosphor sheet is photoelectrically converted to produce image data.

In the present invention, the stimulable phosphor contained in the stimulable phosphor layer formed on the stimulable phosphor sheet may be of any type insofar as it can store radiation energy and can be stimulated by visible light to release the radiation energy stored therein in the form of light. However, a stimulable phosphor which can be stimulated by light having a visible light wavelength is preferably employed. More specifically, preferably employed stimulable phosphors include alkaline earth metal fluorohalide phosphors $(Ba_{1-x}M^{2+}_x)FX:yA$ (where $M^{2+}$ is at least one alkaline earth metal selected from the group consisting of Mg, Ca, Sr, Zn and Cd; X is at least one halogen selected from the group consisting of Cl, Br and I, A is at least one element selected from the group consisting of Eu, Tb, Ce, Tm, Dy, Pr, He, Nd, Yb and Er; x is equal to or greater than 0 and equal to or less than 0.6 and y is equal to or greater than 0 and equal to or less than 0.2.) disclosed in U.S. Pat. No. 4,239,968, alkaline earth metal fluorohalide phosphors SrFX:Z (where X is at least one halogen selected from the group consisting of Cl, Br and I; and Z is at least one of Eu and Ce.) disclosed in Japanese Patent Application Laid Open No. 2-276997, europium activated complex halide phosphors BaFX xNaX':aEu$^{2+}$ (where each of X and X' is at least one halogen selected from the group consisting of Cl, Br and I; x is greater than 0 and equal to or less than 2; and y is greater than 0 and equal to or less than 0.2.) disclosed in Japanese Patent Application Laid Open No. 59-56479, cerium activated trivalent metal oxyhalide phosphors MOX:xCe (where M is at least one trivalent metal selected from the group consisting of Pr, Nd, Pm, Sm, Eu, Tb, Dy, Ho, Er, Tm, Yb and Bi; X is at least one halogen selected from the group consisting of Br and I; and x is greater than 0 and less than 0.1 ) disclosed in Japanese Patent Application Laid Open No. 58-69281, cerium activated rare earth oxyhalide phosphors LnOX:xCe (where Ln is at least one rare earth element selected from the group consisting of Y, La, Gd and Lu; X is at least one halogen selected from the group consisting of Cl, Br, and I; and x is greater than 0 and equal to or less than 0.1.) disclosed in U.S. Pat. No. 4,539,137 and europium activated complex halide phosphors M"FX aM'X'bM"X"$_2$ cM"'X"'$_3$ xA:yEu$^{2+}$ (where M" is at least one alkaline earth metal selected from the group consisting of Ba, Sr and Ca; M' is at least one alkaline metal selected from the group consisting of Li, Na, K, Rb and Cs; M'" is at least one divalent metal selected from the group consisting of Be and Mg; M"' is at least one trivalent metal selected from the group consisting of Al, Ga, In and Tl; A is at least one metal oxide; X is at least one halogen selected from the group consisting of Cl, Br and I; each of X', X" and X"' is at least one halogen selected from the group consisting of F, Cl, Br and I; a is equal to or greater than 0 and equal to or less than 2; b is equal to or greater than 0 and equal to or less than $10^{-2}$; c is equal to or greater than 0 and equal to or less than $10^{-2}$; a+b+c is equal to or greater than $10^{-2}$; x is greater than 0 and equal to or less than 0.5; and y is greater than 0 and equal to or less than 0.2.) disclosed in U.S. Pat. No. 4,962,047.

In the present invention, the chemiluminescent substance may be of any type insofar as it can be used for the chemiluminescent detecting method. However, dioxetanes such as luminol, luxygenin, acridinium ester, AMPPD (adamantyl-1,2-dioxetane), "CDP-Star" (registered trademark) produced by and available from TROPIX, 47 Wiggins Avenue, Bedford, Mass. 01730, U.S.A., "CDP" (registered trademark) produced by and available from TROPIX and the like are preferably used for the present invention.

In the present invention, the labeling substance which produces chemiluminescence by the contact between itself and the chemiluminescent substance may be of any type insofar as it can be used for the chemiluminescent detecting method but catalysts and enzymes are preferably used. Specific examples of catalysts include various metals and such species as adenosine triphosphate and the like. Specific examples of enzymes include lactate dehydrogenase, luciferase, peroxidase and phosphatase such as alkaline phosphatase and the like. Among them, enzymes are preferable, phosphatase is particularly preferable, and alkaline phosphatase is most preferable.

In the present invention, a labeling substance for labeling DNA or RNA complimentary to the target DNA or RNA can be used for determining the base sequence of a nucleic acid such as DNA, RNA or the like obtained by electrophoresis, screening genes obtained by electrophoresis or colony hybridization, producing reference data regarding genes obtained by dot-blotting, and the simple detection of gene amount and expression amount. Specific examples of such labeling substances include digoxigenin (DIG), avidin, streptoavidin, biotin, fluorescein and the like.

In the present invention, in the case where X-rays are used as the radiation for uniformly irradiating the stimulable sheet, the energy thereof is preferably equal to or less than 20 KV and more preferably equal to or less than 12.5 KV. When the energy of the X-rays projected onto the stimulable phosphor sheet exceeds 20 KV, the energy of the X-rays is uniformly stored even in deep portions of the stimulable phosphor layer of the stimulable phosphor sheet. When the stimulable phosphor sheet is thereafter exposed to weak chemiluminescent light, the X-ray energy stored in the deep portions of the stimulable phosphor layer cannot be released. This lowers the detecting accuracy.

In the present invention, in the case where electron beams are used as radiation for uniformly irradiating the stimulable sheet, the energy thereof is preferably equal to or less than 100 KV. Within this range the preferable energy of the electron beams depends on the thickness of the stimulable phosphor layer and whether or not a protective layer is provided. In the case where a stimulable phosphor layer having a thickness of about 50 microns and no protective layer is uniformly irradiated with electron beams whose energy is 150 to 200 KV, the electron beams transmit through the stimulable phosphor layer and the electron ray energy is uniformly stored even in the deep portions of the stimulable phosphor layer. The energy of electron beams stored in the deep portions of the stimulable phosphor layer cannot be released by weak chemiluminescent light. On the other hand, in the case where a stimulable phosphor layer having a thickness of about 50 to 150 microns and no protective layer is uniformly irradiated with electron beams whose energy is equal to or less than 100 KV, the electron ray energy is uniformly stored only in the vicinity of the surface of the stimulable phosphor layer. The electron ray energy stored in the stimulable phosphor layer thereafter can be released, even if the stimulable phosphor sheet is exposed to weak chemiluminescent light. The detecting accuracy of chemiluminescence is therefore enhanced. In the case where the stimulable phosphor sheet has a thickness of 50 to 150 microns and is provided with a protective layer, the energy of electron beams uniformly projected onto the stimulable phosphor layer is preferably equal to or greater than 60 KV.

The sensitizing agent used for the preferred embodiment of the present invention may be of any type insofar as it can convert the wavelength of emitted chemiluminescent light to a wavelength which can efficiently erase the radiation energy stored in the stimulable phosphor layer. However, in the case where phosphors of barium fluorohalide are used as stimulable phosphors, a sensitizing agent containing poly-[vinylbenzyl (benzyl dimethyl ammonium chloride)] shown by the following general formula (1) as a main component is preferably used.

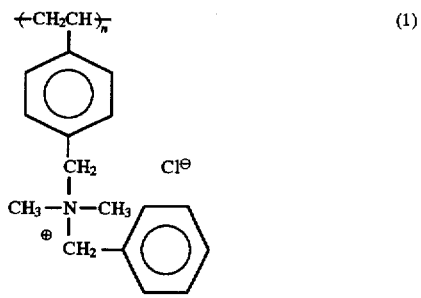

(1)

In the present invention, the sensitizing agent preferably contains a very small amount of fluorescent dye. In the case where the sensitizing agent containing poly-[vinylbenzyl (benzyl dimethyl ammonium chloride)] as a main component is employed, the sensitizing agent preferably contains Fluorescein [Cl-45350 Acid Yellow 73, Dye No. 54101: "Dye Handbook" (Kodan-sha)] shown by the following formula (2) or Sulforhodamine [Dye No. 54012: "Dye Handbook" (Kodan-sha)] shown by the following formula (3).

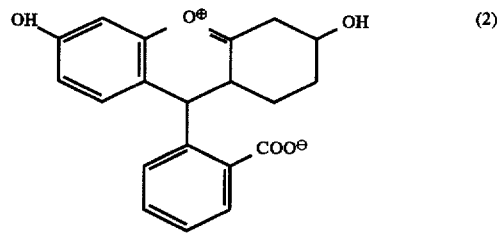

(2)

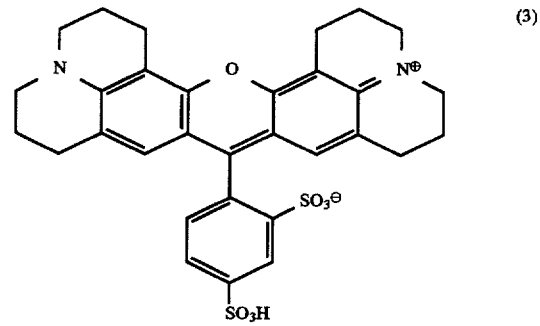

(3)

In the present invention, the sensitizing agent preferably contains a small amount of a surface active agent. In the case where the sensitizing agent containing poly-[vinylbenzyl (benzyl dimethyl ammonium chloride)] as a main component is employed, the sensitizing agent preferably contains an anionic dodecyloxy-polyoxyethylene sulfate sodium salt, $C_{12}H_{25}O(CH_2CH_2O)_nSO_3Na$.

In the present invention, the sensitizing agent preferably contains a small amount of inorganic substance. In the case where the sensitizing agent containing poly-[vinylbenzyl (benzyl dimethyl ammonium chloride)] as a main component is employed, the sensitizing agent preferably contains NaCl or inorganic cations such as Na, Ca, Al, K, Ti and the like as inorganic substances. In the case where inorganic cations are contained, the amount of Na, Ca or Al is preferably greater than the amount of K or Ti.

In the present invention, in the case where the sensitizing agent containing poly-[vinylbenzyl (benzyl dimethyl ammonium chloride)] as a main component is employed, the sensitizing agent preferably contains a small amount of sodium acetate.

Specifically, "EMERALD" or "RUBY" produced by and available from TROPIX, 47 Wiggins Avenue, Bedford, Mass. 01730, U.S.A. is preferably used as the sensitizing agent. The "EMERALD" and "RUBY" produced by TROPIX contain poly-[vinylbenzyl (benzyl dimethyl ammonium chloride)] shown by the general formula (1) as a main component. The "EMERALD" produced by TROPIX contains a very small amount of Fluorescein [CI-45350 Acid Yellow 73, Dye No. 54101: "Dye Handbook" (Kodan-sha)] shown by the formula (2), a small amount of anionic dodecyloxy-polyoxyethylene sulfate sodium salt, $C_{12}H_{25}O(CH_2CH_2O)_nSO_3Na$, a small amount of NaCl and a small amount of sodium acetate. The "RUBY" produced by TROPIX contains a very small amount of Sulforhodamine [Dye No. 54012: "Dye Handbook" (Kodan-sha)] shown by the formula (3), a small amount of anionic dodecyloxy-polyoxyethylene sulfate sodium salt, $C_{12}H_{25}O(CH_2CH_2O)_nSO_3Na$, a small amount of inorganic cations such as Na, Ca, Al, K, Ti and the like and a small amount of sodium acetate.

The above and other objects and features of the present invention will become apparent from the following description made with reference to the accompanying drawings.

BRIEF DESCRIPTION OF THE DRAWINGS

FIGS. 3A and 3B is a flow sheet showing the procedure of a chemiluminescent detecting method which is another embodiment of the present invention.

FIGS. 5A and 5B is a flow sheet showing the procedure of a chemiluminescent detecting method which is a further embodiment of the present invention.

DESCRIPTION OF THE PREFERRED EMBODIMENTS

Figures 1A, 1B:
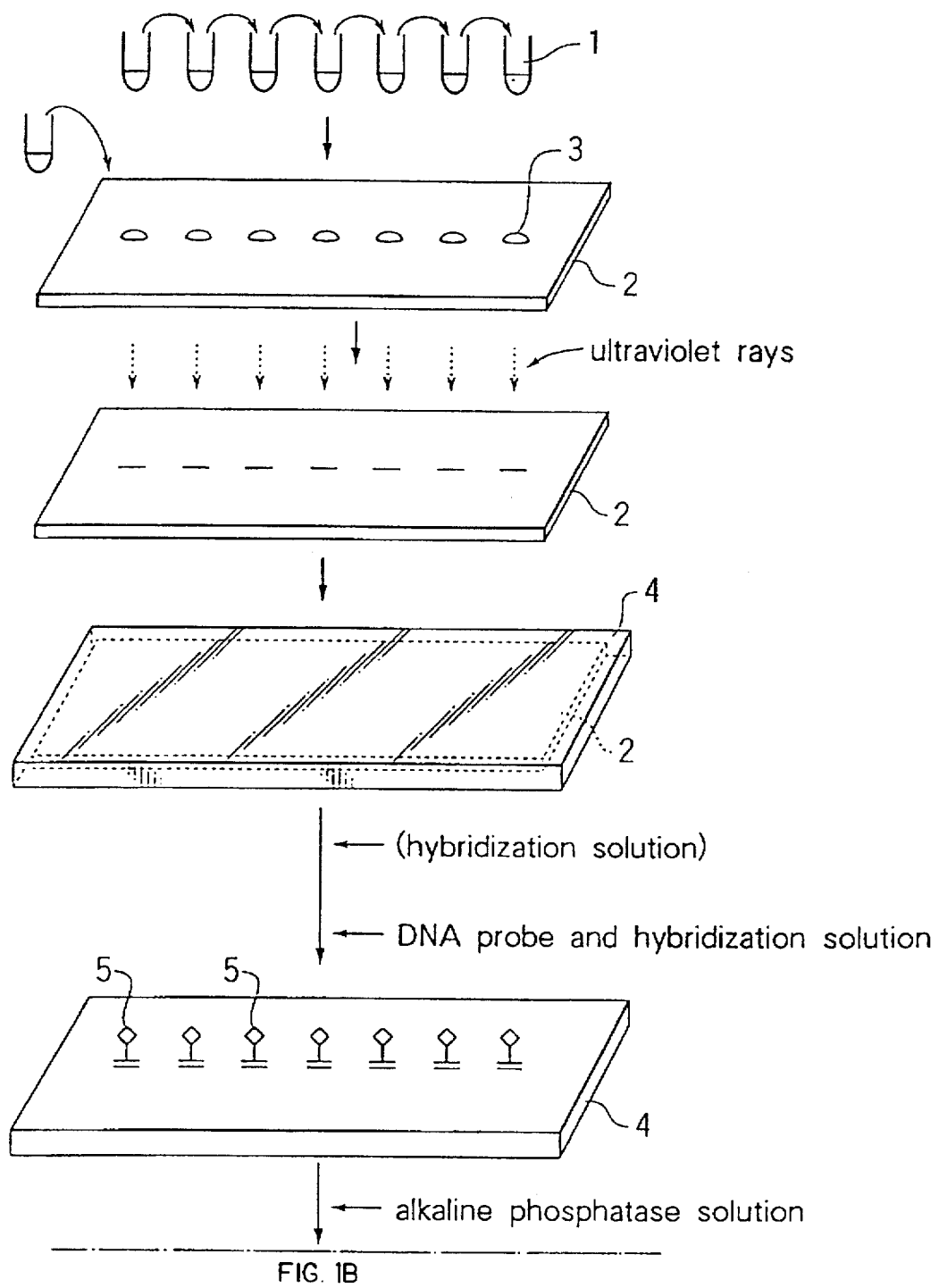
FIGS. 1A and 1B is a flow sheet showing the procedure of a chemiluminescent detecting method which is an embodiment of the present invention.

FIG. 1A shows a chemiluminescent detecting method for detecting an amount of genes produced by dot-blotting and producing reference data regarding genes.

As shown in FIG. 1A, a dilution series 1 of seven diluted solutions of unlabeled DNA is produced. For example, the respective members of the dilution series 1 contain 10 ng/microliter, 1 ng/microliter, 100 pg/microliter, 10 pg/microliter, 1 pg/microliter, 100 fg/microliter and 10 fg/microliter of DNA.

Then, the respective diluted solutions of DNA are dropped on a membrane filter 2 made of nylon to form spots 3.

After drying, the membrane filter 2 is irradiated with ultraviolet rays so that the DNA and the membrane filter 2 are cross-linked to fix DNA onto the membrane filter 2.

Thereafter, the membrane filter 2 to which DNA has been fixed is accommodated in a hybridization bag 4 made of plastic which can transmit visible light and be sealed.

Then, a hybridization solution is prepared and poured into the hybridization bag 4 to effect pre-hybridization.

On the other hand, a complementary DNA probe labeled with digoxigenin (DIG)-dNTP is prepared and added to the hybridization solution. After the hybridization solution for pre-hybridization has been discharged from the hybridization bag 4, the thus prepared solution is added into the hybridization bag 4 to hybridize the complementary DNA and the DNA fixed on the membrane filter 2. In FIG 1A, the reference numeral 5 designates DNA hybridized with the complementary DNA. Since this embodiment is directed to detecting an amount of genes and producing reference data regarding genes, all DNA dropped on the membrane filter 2 is hybridized with the complementary DNA.

After the completion of the hybridization, the membrane filter 2 is washed. Further, an antidigoxigenin-alkaline phosphatase labeling antibody solution is prepared and added into the hybridization bag 4. As a result, the complementary DNA labeled with digoxigenin (DIG) and the alkaline phosphatase are linked, whereby the DNA is labeled. In FIG. 1B, the reference numeral 6 designates the complementary DNA labeled with an alkaline phosphatase. In this embodiment, all complementary DNA hybridized with DNA is labeled with alkaline phosphatase.

After the antidigoxigenin-alkaline phosphatase labeling antibody solution has been discharged from the hybridization bag 4, an AMPPD (adamantyl-1,2-dioxetane) solution is added into the hybridization bag 4. It is a property of the AMPPD to dissolve and emit chemiluminescent light when it comes into contact with alkaline phosphatase, and, therefore, the DNA labeled with alkaline phosphatase emits chemiluminescent light.

On the other hand, the surface of a stimulable phosphor sheet 7 formed with a stimulable phosphor layer containing a stimulable phosphor of barium fluorobromide which can store the energy of radiation, is uniformly irradiated with X-rays so as to uniformly store the energy of low energy X-rays in the stimulable phosphor layer. The wavelength of the chemiluminescent light produced by the dissolution of AMPPD is about 470 nm, whereas the peak wavelength for stimulating a stimulable phosphor of barium fluorobromide used in the autoradiographic detecting method lies on the higher wavelength side. Therefore, for efficiently detecting chemiluminescent light, it is preferable to select the stimulable phosphor sheet 7 from among those used in the autoradiographic detecting method formed with a stimulable phosphor layer containing a stimulable phosphor of barium fluorobromide whose peak stimulation wavelength is shorter. In the case where the stimulable phosphor of barium fluorobromide is used, the peak stimulation wavelength can be shifted to the shorter side by increasing the amount of bromide.

After a part of the AMPPD solution has been discharged from the hybridization bag 4, the hybridization bag 4 is heated for increasing the dissolving speed of the AMPPD and the stimulable phosphor sheet 7 formed with a stimulable phosphor layer which uniformly stores the energy of low energy X-rays in the above described manner and the hybridization bag 4 are brought into surface contact with each other in a darkroom.

In this embodiment, the stimulable phosphor of barium fluorohalide which can store the energy of radiation and be stimulated by an electromagnetic wave whose wavelength lies within that of visible light is employed. Therefore, when the stimulable phosphor layer formed on the stimulable phosphor sheet 7 is exposed to chemiluminescent light produced by the dissolution of the AMPPD, the X-ray energy stored in portions of the stimulable phosphor layer exposed to the chemiluminescent light is released.

After a predetermined time period has passed, the stimulable phosphor sheet 7 is removed from the hybridization bag 4. Thus, the X-ray energy is uniformly stored in only portions of the stimulable phosphor layer of the stimulable phosphor sheet 7 which were not exposed to the chemiluminescent light, while the X-ray energy stored in portions of the stimulable phosphor layer which were exposed to the chemiluminescent light has been released and erased in accordance with the intensity of the chemiluminescent light. In this embodiment, images corresponding to the DNA density of the respective spots 3 are stored and recorded in positions of the stimulable phosphor layer corresponding to the respective spots 3.

Figure 2:
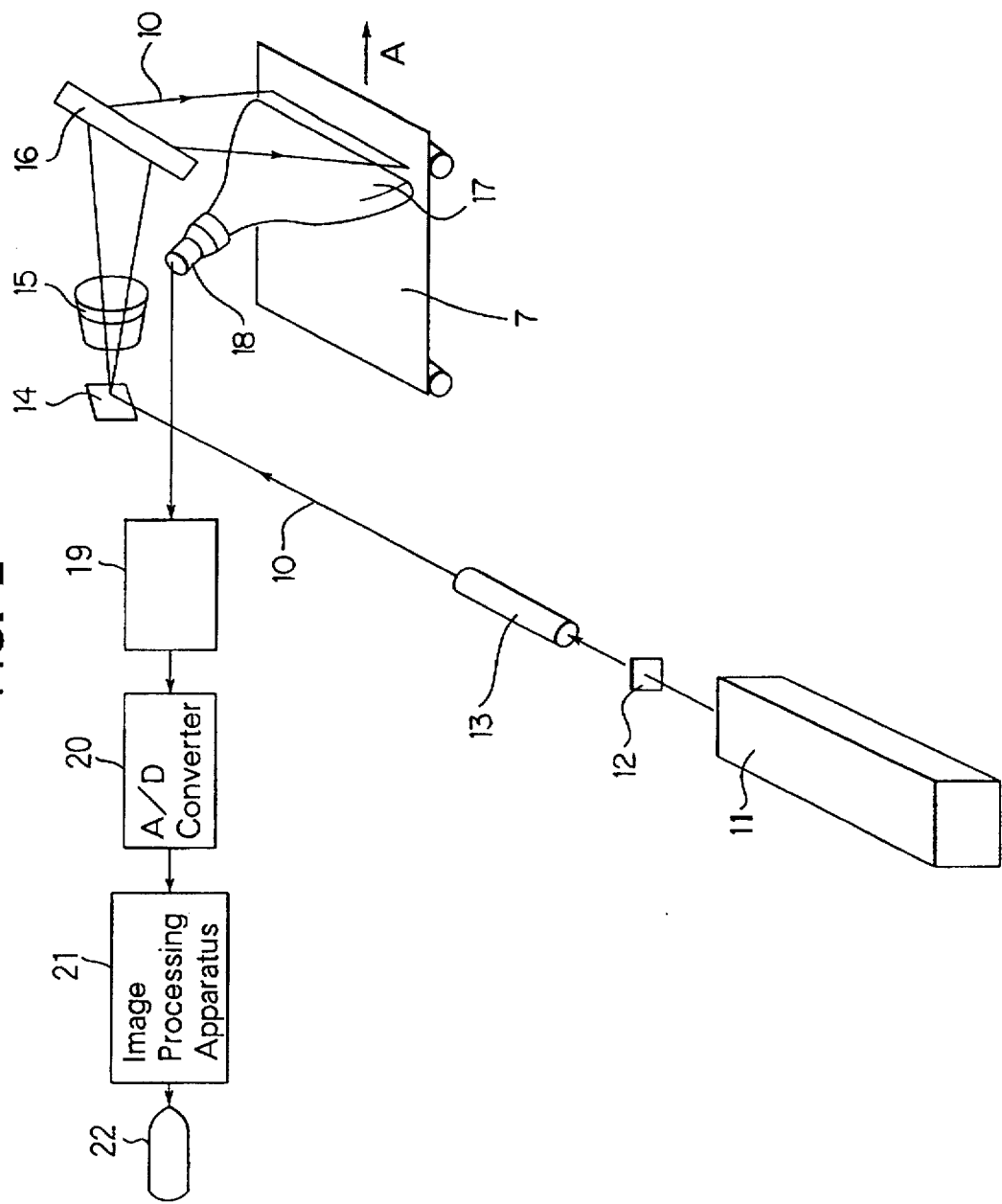
FIG. 2 is a schematic perspective view showing one example of an image data, reading apparatus and an image processing apparatus.

FIG. 2 is a schematic perspective view showing one example of an image data reading apparatus for reading image data from the stimulable phosphor sheet 7 formed with the stimulable phosphor layer in which images are stored and recorded and an image processing apparatus.

The image data reading apparatus is constituted so as to scan the stimulable phosphor sheet 7 with a laser beam 10 and stimulate it, thereby causing it to emit stimulated emission.

The laser beam 10 is generated by a laser beam source 11 and passes through a filter 12 to cut off light in the wavelength region corresponding to the wavelength region of stimulated emission to be emitted from the stimulable phosphor sheet 7 in response to stimulation by the laser beam 10. The beam diameter of the laser beam 10 is accurately adjusted by a beam expander 13 and the laser beam 10 enters a beam deflector 14 such as a galvanometer. The laser beam 10 deflected by the beam deflector 14 passes through an fθ lens 15 and is reflected by a plane reflecting mirror 16, thereby impinging upon the stimulable phosphor sheet 7. The fθ lens 15 ensures that the stimulable phosphor sheet 7 is always scanned with the laser beam 10 at a uniform beam speed.

The stimulable phosphor sheet 7 is conveyed in the direction of the arrow A in FIG. 2 in synchronism with the above mentioned scanning with the laser beam 10 so that the whole surface of the stimulable phosphor sheet 7 is scanned by the laser beam 10.

When irradiated with the laser beam 10, the stimulable phosphor sheet 7 releases stimulated emission in an amount proportional to the radiation energy stored therein and the stimulated emission enters a light guiding sheet 17.

The light receiving end of the light guiding sheet 17 has a linear shape and is positioned in the vicinity of the stimulable phosphor sheet 7 so as to face the scanning line on the stimulable phosphor sheet 7. The exit end of the light guiding sheet 17 is in the form of a ring and is connected to the light receiving surface of a light detector 18 such as a photomultiplier for photoelectrically detecting light. This light guiding sheet 17 is made by processing a sheet of a transparent thermoplastic resin such as an acrylic synthetic resin and so constituted that the emission introduced from the light receiving end is transmitted to the exit end under repeated total reflection within the light guiding sheet 17 and received by the light receiving surface of the light detector 18 via the exit end.

Therefore, the stimulated emission produced by the stimulable phosphor sheet 7 upon being irradiated with the laser beam 10 enters into the light guiding sheet 17 and is received by the light detector 18 via the exit end under repeated total reflection within the sheet 17.

On the light receiving surface of the light detector 18 is provided a filter which allows only light of the wavelength region of the stimulated emission released from the stimulable phosphor sheet 7 to pass through and cuts off light of the wavelength region of the laser beam so that the light detector 18 can photoelectrically detect only the stimulated emission released from the stimulable phosphor sheet 7.

The stimulated emission photoelectrically detected by the light detector 18 is converted to an electrical signal, amplified by an amplifier 19 having a predetermined amplifying factor so as to produce an electrical signal of a predetermined level and then input to an A/D converter 20. The electrical signal is converted to a digital signal with a scale factor suitable for the signal fluctuation width and input to an image processing apparatus 21. The digital signal is stored in an image data memory (not shown) and an image is displayed on the screen of a CRT 22 after being subjected to predetermined image processing as the occasion demands.

According to the above described embodiment, the stimulable phosphor layer containing the stimulable phosphor of barium fluorohalide which can be used in the autoradiographic detecting method but cannot absorb visible light, is uniformly irradiated with X-rays having a low energy to store the energy of X-rays uniformly therein, and the X-ray energy stored in the stimulable phosphor layer is released by the chemiluminescent light produced by the dissolution of the AMPPD, thereby storing images corresponding to the DNA density of the respective spots in the stimulable phosphor layer. Then, the stimulable phosphor layer of the stimulable phosphor sheet 7 is scanned with the laser beam to emit stimulated emission, the stimulated emission is photoelectrically detected by the light detector 18, and after the obtained signals have been converted to digital signals and the digital signals have been stored in an image memory, predetermined digital image processing is effected as the occasion demands and displayed on the screen of the CRT 22. Therefore, since it is unnecessary to keep the stimulable phosphor sheet constantly shielded from visible light, the stimulable phosphor sheet can be easily handled. Further, since the stimulable phosphor sheet 7 can be used for both the chemiluminescent detecting method and the autoradiographic detecting method used for the same purpose as the chemiluminescent detecting method and images stored in the stimulable phosphor sheet 7 can be easily converted to digital signals, it is possible to very effectively detect the chemiluminescence with high accuracy. Moreover, since the stimulable phosphor sheet 7 formed with the stimulable phosphor layer containing the stimulable phosphor of barium fluorobromide rich in bromide is used in this embodiment, it is possible to more efficiently detect the chemiluminescence.

FIGS. 3A and 3B is a flow sheet showing the procedure of a chemiluminescent detecting method which is another embodiment of the present invention.

In this embodiment, the amount of genes produced by dot-blotting is detected and reference data regarding genes are produced similarly to in the above described embodiment and the procedure is the same as that of the above described embodiment except that the AMPPD contains "RUBY" produced by and available from TROPIX, 47 Wiggins Avenue, Bedford, Mass. 01730, U.S.A. as a sensitizing agent and that the surface of the stimulable phosphor sheet 7 is uniformly irradiated with X-rays having an energy equal to or less than 20 KV.

The "RUBY" produced by TROPIX contains poly-[vinylbenzyl (benzyl dimethyl ammonium chloride)] shown by the following general formula (1) as a main component and further contains a very small amount of Sulforhodamine [Dye No. 54012: "Dye Handbook" (Kodan-sha)] which is a fluorescent dye and shown in the following general formula (3), a small amount of an anionic dodecyloxy-polyoxyethylene sulfate sodium salt, $C_{12}H_{25}O(CH_2CH_2O)_nSO_3Na$, which is a surface active agent, a small amount of inorganic cations such as Na, Ca, Al, K, Ti and the like, and a small amount of sodium acetate.

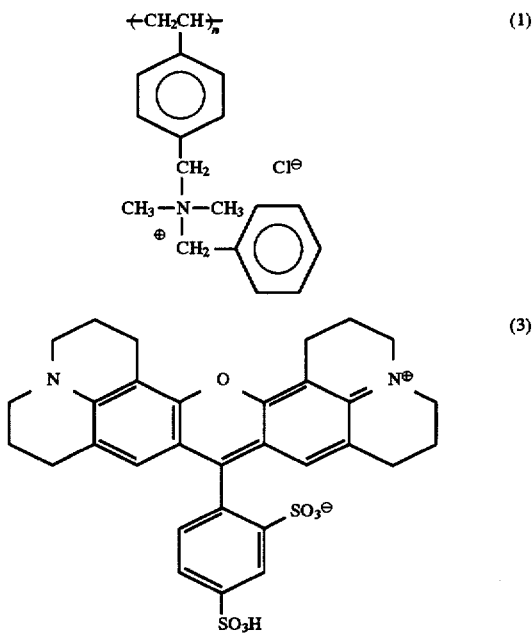

Although the wavelength of light which can most efficiently erase the X-ray energy stored in the stimulable phosphors of barium fluorohalide is about 580 nm, the wavelength of the chemiluminescent light produced by the dissolution of the AMPPD is about 470 nm. However, since the AMPPD solution contains the "RUBY" produced by TROPIX as a sensitizing agent, the wavelength of the chemiluminescent light produced by the dissolution of the AMPPD is converted to 620 nm. Therefore, it is possible to efficiently erase the X-ray energy stored in the stimulable phosphor.

In this embodiment, the surface of the stimulable phosphor sheet 7 is uniformly irradiated with X-rays having an energy equal to or less than 20 KV. This is because almost all of the X-ray energy stored in the stimulable phosphor layer formed on the stimulable phosphor sheet 7, can be released and erased by weak chemiluminescent light when the X-ray energy is stored in the stimulable phosphors, only in the vicinity of the surface of the stimulable phosphor sheet 7. It therefore improves the detecting accuracy of the chemiluminescence. More specifically, when the surface of the stimulable phosphor sheet 7 is irradiated with high energy X-rays, the X-ray energy is stored in the stimulable phosphors not only in the vicinity of the surface of the stimulable phosphor sheet 7 but also in deep portions of the layer and it is difficult to sufficiently release and erase the X-ray energy uniformly stored in the stimulable phosphor layer by exposing the stimulable phosphor layer to weak chemiluminescent light. The detecting accuracy of the chemiluminescence is therefore lowered. On the contrary, when the surface of the stimulable phosphor sheet 7 is irradiated with low energy X-rays, the X-ray energy is stored in the stimulable phosphors only in the vicinity of the surface of the stimulable phosphor sheet 7. Since almost all of the X-ray energy stored in the stimulable phosphor layer formed on the stimulable phosphor sheet 7 can be therefore released and erased by weak chemiluminescent light, chemiluminescent images can be recorded in the stimulable phosphor sheet 7 with high sensitivity. It was experimentally confirmed that the energy of the X-rays with which the surface of the stimulable phosphor sheet 7 is irradiated is preferably equal to or less than 20 KV.

Images corresponding to the DNA density of the respective spots 3 stored in the stimulable phosphor layer formed on the stimulable phosphor sheet 7 are read in the same manner as in the previously described embodiment and converted to digital signals to be displayed on the screen of the CRT 22 as images.

According to this embodiment, since the stimulable phosphor layer containing a stimulable phosphor of barium fluorobromide is uniformly irradiated with low energy X-rays having an energy equal to or less than 20 KV to store the X-ray energy therein, the X-ray energy is stored in the stimulable phosphor layer only in the vicinity of the surface thereof and, therefore, even if the stimulable phosphor layer is exposed to only weak chemiluminescent light, almost all of the X-ray energy uniformly stored in the stimulable phosphor layer at the exposed portions can be released and erased, whereby it is possible to record chemiluminescent images with high sensitivity. Therefore, the detecting accuracy of the chemiluminescence can be improved. Further, in this embodiment, since the AMPPD contains "RUBY" produced by TROPIX and the wavelength of the chemiluminescent light produced by the dissolution of the AMPPD is changed from about 470 nm to 620 nm which can efficiently erase the X-ray energy stored in the stimulable phosphor layer containing the stimulable phosphor of barium fluorobromide, it is possible to more efficiently detect chemiluminescence using the stimulable phosphor.

Figures 4A, 4B:
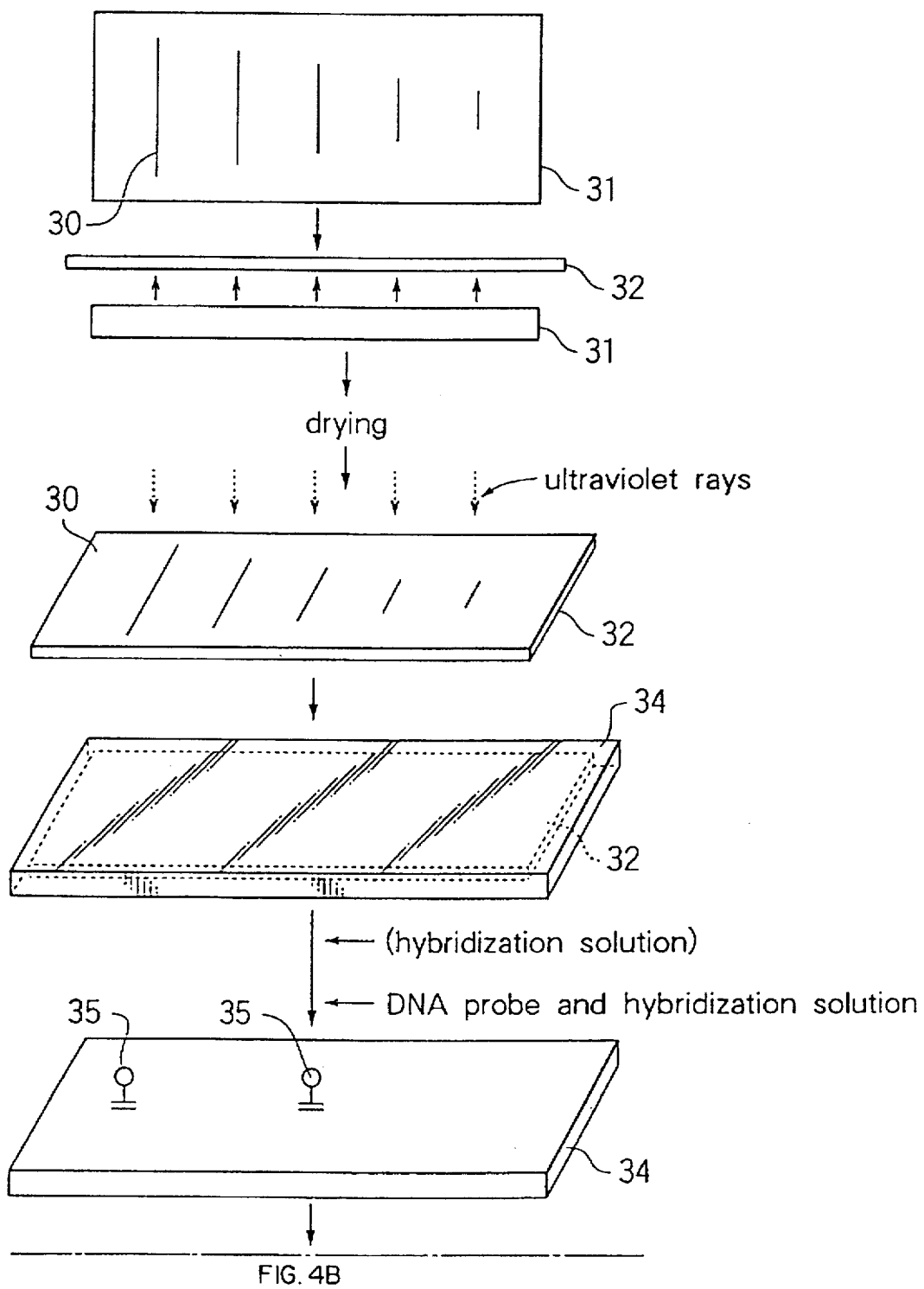
FIGS. 4A and 4B is a flow sheet showing the procedure of a chemiluminescent detecting method which is a further embodiment of the present invention.

FIGS. 4A and 4B is a flow sheet showing the procedure of a chemiluminescent detecting method which is a further embodiment of the present invention.

In the embodiment shown FIGS. 4A and 4B, DNA sequence is determined by the Southern blotting method.

In FIG. 4A, DNA fragments 30 containing a target gene are first separated and distributed on an agarose gel support medium 31 by electrophoresis.

Then, as well known, the DNA fragments 30 separated and distributed on the agarose gel support medium 31 are denatured by alkaline processing and the agarose gel support medium 31 and a membrane filter 32 made of nylon are placed in layers for a predetermined time period, thereby transferring the denatured DNA fragments 30 onto the membrane filter 32.

Thereafter, the membrane filter 32 is dried and irradiated with ultraviolet rays to cross-link the DNA and the membrane filter 32 to fix the DNA onto the membrane filter 32.

Then, the membrane filter 32 onto which the DNA is fixed is accommodated in a hybridization bag 34 made of plastic which can transmit visible light and be sealed.

Then, a hybridization solution is prepared and poured into the hybridization bag 34 to effect pre-hybridization.

On the other hand, a complementary DNA probe labeled with digoxigenin (DIG)-dNTP and containing the target DNA is prepared and is added to the hybridization solution.

After the hybridization solution for prehybridization has been discharged from the hybridization bag 34, the thus prepared solution is added into the hybridization bag 34 to hybridize the complementary DNA and the DNA fixed onto the membrane filter 32. In FIG. 4, the reference numeral 35 designates the target DNA hybridized with the complementary DNA.

After the completion of the hybridization, the membrane filter 32 is washed. Further, an antidigoxigenin-alkaline phosphatase labeling antibody solution is prepared and added into the hybridization bag 34. As a result, the complementary DNA labeled with digoxigenin (DIG) and the alkaline phosphatase are linked, whereby the DNA is labeled. In FIG. 4, the reference numeral 36 designates the complementary DNA labeled with an alkaline phosphatase.

After the antidigoxigenin-alkaline phosphatase labeling antibody solution has been discharged from the hybridization bag 34, an AMPPD solution is added into the hybridization bag 34. As a result, chemiluminescent light is emitted from positions where the DNA labeled with alkaline phosphatase is present. The AMPPD contains "EMERALD" produced by and available from TROPIX, 47 Wiggins Avenue, Bedford, Mass. 01730, U.S.A. as a sensitizing agent.

The "EMERALD" produced by TROPIX contains poly-[vinylbenzyl (benzyl dimethyl ammonium chloride)] shown by the general formula (1) as a main component and further contains a very small amount of Fluorescein [Cl-45350 Acid Yellow 73, Dye No. 54101: "Dye Handbook" (Kodan-sha)], which is a fluorescent dye shown by the following general formula (2), a small amount of an anionic dodecyloxy-polyoxyethylene sulfate sodium salt, $C_{12}H_{25}O(CH_2CH_2O)_n SO_3Na$, which is a surface active agent, a small amount of NaCl, and a small amount of sodium acetate.

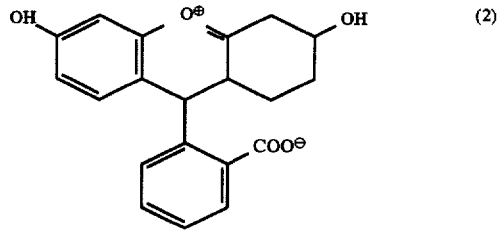

(2)

On the other hand, the surface of a stimulable phosphor sheet 37 formed with a stimulable phosphor layer containing a stimulable phosphor of barium fluorobromide which can store the energy of radiation is uniformly irradiated with low energy electron beams so as to uniformly store the energy of low energy electron beams in the stimulable phosphor layer.

After a part of the AMPPD solution has been discharged from the hybridization bag 34, the hybridization bag 34 is heated for increasing the dissolving speed of the AMPPD and the stimulable phosphor sheet 37 formed with a stimulable phosphor layer which uniformly stores the energy of low energy electron beams in the above described manner and the hybridization bag 34 are caused to come into surface contact with each other in a darkroom.

As a result, the energy of low energy electron beams stored in portions of the stimulable phosphor layer which are exposed to chemiluminescent light produced by the dissolution of the AMPPD is released and erased, whereby images of the DNA are recorded in the stimulable phosphor layer.

In this embodiment, the surface of the stimulable phosphor sheet 37 is uniformly irradiated with electron beams of low energy. This is because almost all of the electron beam energy stored in the stimulable phosphor layer formed on the stimulable phosphor sheet 37 can be released and erased by weak chemiluminescent light when the electron beam energy is stored in the stimulable phosphor only in the vicinity of the surface of the stimulable phosphor sheet 37. Irradiation with low energy electron beams therefore improves the detecting accuracy of chemiluminescence. More specifically, when the surface of the stimulable phosphor sheet 37 is irradiated with high energy electron beams, the electron beam energy is stored in the stimulable phosphor not only in the vicinity of the surface of the stimulable phosphor sheet 37 but also in deep portions of the layer and it is difficult to sufficiently release and erase the electron beam energy uniformly stored in the stimulable phosphor layer by exposing the stimulable phosphor layer to weak chemiluminescent light. The detecting accuracy of chemiluminescence is therefore lowered. On the contrary, when the surface of the stimulable phosphor sheet 37 is irradiated with low energy electron beams, the electron beam energy is stored in the stimulable phosphor only in the vicinity of the surface of the stimulable phosphor sheet 37. Since almost all of the electron beam energy stored in the stimulable phosphor layer formed on the stimulable phosphor sheet 37 can be therefore released and erased by weak chemiluminescent light, chemiluminescent images can be recorded in the stimulable phosphor sheet 37 with high sensitivity. The preferable energy of the electron beams with which the surface of the stimulable phosphor sheet 37 is uniformly irradiated depends on the thickness of the stimulable phosphor layer and whether or not a protective layer is provided, and in the case where the thickness of the stimulable phosphor layer is in the range of about 50 to 150 microns and no protective layer is provided, the energy of the electron beams is preferably equal to or less than 100 KV.

Although the wavelength of light which can most efficiently erase the energy of electron beams stored in the stimulable phosphor of barium fluorohalide is about 580 nm, the wavelength of the chemiluminescent light produced by the dissolution of the AMPPD is about 470 nm. However, since the AMPPD solution contains the "EMERALD" produced by and available from TROPIX as a sensitizing agent, the wavelength of the chemiluminescent light produced by the dissolution of the AMPPD is converted to 540 nm. Therefore, it is possible to efficiently erase the electron beam energy stored in the stimulable phosphor.

After a predetermined time period has passed, the stimulable phosphor sheet 37 is removed from the hybridization bag 34. Thus, the electron beam energy is uniformly stored in only portions of the stimulable phosphor layer of the stimulable phosphor sheet 37 which were not exposed to the chemiluminescent light, while the electron beam energy stored in portions of the stimulable phosphor layer which were exposed to the chemiluminescent light has been released and erased in accordance with the intensity of the chemiluminescent light, whereby images of the DNA are recorded.

The DNA images recorded in the stimulable phosphor layer of the stimulable phosphor sheet 37 are read as digital signals by the image data reading apparatus and the digital signals are fed to the image processing apparatus 21 where they are stored in the image data memory. After being subjected to digital image processing, they are displayed as images on the screen of the CRT 22. It is possible to determine the sequence of the DNA based on the images displayed on the screen of the CRT 22.

In this embodiment, as in the second described embodiment, it is possible to very efficiently detect chemiluminescence with high accuracy. Further, in this embodiment, since the stimulable phosphor layer containing a stimulable phosphor of barium fluorobromide is uniformly irradiated with low energy electron beams to store the energy of the electron beams therein, the electron beam energy is stored in the stimulable phosphor layer only in the vicinity of the surface thereof and, therefore, even if the stimulable phosphor layer is exposed to only weak chemiluminescent light, almost all of the electron beam energy uniformly stored in the stimulable phosphor layer at the exposed portions can be released and erased, whereby it is possible to record chemiluminescent images with high sensitivity. Therefore, the detecting accuracy of the chemiluminescence can be improved. Further, in this embodiment, the AMPPD contains "EMERALD" produced by TROPIX and the wavelength of the chemiluminescent light produced by the dissolution of the AMPPD is changed from about 470 nm to 540 nm. As 540 nm light can efficiently erase the electron beam energy stored in the stimulable phosphor layer containing the stimulable phosphor of barium fluorobromide, it is possible to more efficiently detect chemiluminescence using the stimulable phosphor.

FIG. 5 is a flow sheet showing the procedure of a chemiluminescent detecting method which is a further embodiment of the present invention.

In this embodiment, DNA sequence is determined by the Southern blotting method similarly to the above described embodiment shown in FIGS. 4A and 4B and the procedure is the same as in the above described embodiment shown in FIGS. 4A and 4B except the surface of the stimulable phosphor sheet 7 is uniformly irradiated with ultraviolet rays to store the energy of ultraviolet rays in the stimulable phosphor layer.

In this embodiment, as in the second and third described embodiments, it is possible to very efficiently detect chemiluminescence with high accuracy.

For further clarifying the technical advantages of the present invention, working Examples will now be described.

EXAMPLE 1

First, a dilution series of seven diluted solutions of unlabeled DNA was prepared so that the respective members of the dilution series contained 10 ng/microliter of DNA, 1 ng/microliter of DNA, 100 pg/microliter of DNA, 10 pg/microliter of DNA, 1 pg/microliter of DNA, 100 fg/microliter of DNA and 10 fg/microliter of DNA.

Then, a pipet was used to drop the respective dilution sequences on a 15 cm×10 cm membrane filter made of nylon having a pore diameter of 0.45 microns, thereby forming spots.

After drying, the membrane filter was irradiated with ultraviolet rays having a wavelength of about 265 nm so that the DNA and the membrane filter were cross-linked with each other and the DNA was fixed onto the membrane filter.

Then, the membrane filter on which the DNA was fixed was dampened with sterilized water and was accommodated in a hybridization bag made of plastic which was able to transmit visible light and to be sealed.

Afterward, 30 milliliters of a hybridization solution containing 500 millimole of sodium phosphate buffer solution (pH 7.2), 7% of SDS and 1 millimole of EDTA was poured into the hybridization bag accommodating the membrane filter on which the DNA was fixed, whereby the prehybridization was effected.

On the other hand, a DNA probe was prepared as follows.

One microgram of DNA fragments was dissolved in 15 microliters of distilled water and the solution was accommodated in a microtube. The microtube was sealed and placed into boiling water to be held at 100° C. for five minutes, whereby the DNA fragments were denatured so as to have a single chain.

The denatured DNA fragments were quickly cooled in ice water for five minutes and deposited by a small centrifugal machine. Then, two microliters of hexanucleotide mixture and two microliters of dNTP labeling substance were added thereto and thoroughly mixed. The dNTP labeling substance contained digoxigenin-dNTP.

One microliter of Klenow enzyme was added to the mixture and the mixture was gently mixed by pipetting, thereby reacted it at 37° C. for two hours.

Then, two microliters of EDTA of two moles/liter was added thereto and the reaction was stopped.

The mixture was further added with 2.5 microliters of potassium chloride of four moles/liter and 75 microliters of 100% ethanol were added thereto and left at –70° C. for one hour, thereby forming deposits.

Then, the microtube was centrifuged with a very small centrifugal machine at 4° C. for ten minutes at 15000 revolutions per minute, thereby collecting deposits at the bottom of the microtube.

After the supernatant portion of the mixture had been sucked off with a pipet, 500 microliters of 70% ethanol was added to the remaining mixture and the tube was violently shaken using a testtube mixer. After it had been confirmed that the deposits had peeled off the bottom of the microtube, the microtube was centrifuged with a very small centrifugal machine at 4° C. for ten minutes at 15000 revolutions per minute, thereby again collecting deposits at the bottom of the microtube.

Then, the supernatant portion of the mixture was sucked off with a pipet and the remaining mixture was dried with air.

Afterward, 50 microliters of TE buffer solution was added thereto to prepare a DNA probe that was preserved at –20° C.

A predetermined amount of the thus prepared DNA probe was placed in another microtube and the microtube was sealed and placed in boiling water to be held at 100° C. for five minutes, whereby the DNA probe was denatured so as to have a single chain.

The thus denatured DNA probe was quickly cooled in ice water for five minutes and deposited.

Then, the corner of the hybridization bag was cut off and the prehybridization solution was discharged from the hybridization bag. The DNA probe was added to ten milliliters of a hybridization solution which had been warmed to 65° C. so that the concentration of the DNA probe became 20 ng/milliliter and the resultant mixture was added into the hybridization bag accommodating the membrane filter onto which the DNA was fixed. The hybridization bag was sealed and hybridization was effected at 65° C. for fifteen hours.

After the completion of the hybridization, the hybridization solution was discharged from the hybridization bag and a warm washing solution containing 40 millimoles of sodium phosphate buffer solution (pH 7.2) and one % of SDS was poured into the hybridization bag. The hybridization bag was sealed and the membrane filter was washed by shaking the hybridization bag. The washing was continued for twenty minutes in three steps with a new washing solution being added to the hybridization bag at the beginning of each step.

After the completion of the washing operation, the washing solution was discharged from the hybridization bag. Further, an antidigoxigenin-alkaline phosphatase labeling antibody solution was prepared and added into the hybridization bag and a complementary DNA labeled with digoxigenin and the alkaline phosphatase were linked so as to label the DNA.

Then, the antidigoxigenin-alkaline phosphatase labeling antibody solution was discharged from the hybridization bag and an AMPPD solution was added into the hybridization bag.

On the other hand, the surface of a stimulable phosphor sheet formed with a stimulable phosphor layer containing a stimulable phosphor of barium fluorobromide was uniformly irradiated with low energy X-rays using an X-ray source of 8 KV and 150 microamperes positioned apart from the surface of the stimulable phosphor sheet by 50 cm so that the low energy of X-rays were stored in the stimulable phosphor layer.

Next, a part of the AMPPD solution was discharged from the hybridization bag, the hybridization bag was heated to 37° C. for increasing the dissolving speed of the AMPPD and the stimulable phosphor sheet formed with the stimulable phosphor layer uniformly storing the energy of low energy X-rays and the hybridization bag were placed in surface-contact with each other for four hours in a darkroom.

Then, the surface of the stimulable phosphor sheet was irradiated with a helium-neon laser beam using the image data reading apparatus shown in FIG. 2 and the stimulated emission was photoelectrically detected and converted to digital signals. When images were reproduced on the screen of the CRT based on the digital signals, the DNA of the 100 fg/microliter series could be detected.

EXAMPLE 2

A dilution series of DNA was reproduced on the screen of the CRT in the same manner as in Example 1 except that a sensitizing agent "EMERALD" produced by and available from TROPIX, 47 Wiggins Avenue, Bedford, Mass. 01730, U.S.A. was added to the AMPPD solution and that the stimulable phosphor sheet formed with the stimulable phosphor layer uniformly storing the energy of low energy X-rays and the hybridization bag were left in surface-contact with each other for three hours in a darkroom. As a result, the DNA of the 100 fg/microliter series could be detected.

EXAMPLE 3

A dilution series of DNA was reproduced on the screen of the CRT in the same manner as in Example 1 except that a sensitizing agent "RUBY" produced by and available from TROPIX, 47 Wiggins Avenue, Bedford, Mass. 01730, U.S.A. was added to the AMPPD solution and that the stimulable phosphor sheet formed with the stimulable phosphor layer uniformly storing the energy of low energy X-rays and the hybridization bag were left in surface-contact with each other for three hours in a darkroom. As a result, the DNA of the 100 fg/microliter series could be detected.

COMPARATIVE EXAMPLE

A dilution series of DNA was reproduced on the screen of the CRT in the same manner as in Example 1 except that the surface of a stimulable phosphor sheet formed with a stimulable phosphor layer containing a stimulable phosphor of barium fluorobromide was uniformly irradiated with X-rays using an X-ray source of 80 KV and 150 microamperes positioned apart from the surface of the stimulable phosphor sheet by 50 cm so that the energy of X-rays were stored in the stimulable phosphor layer. As a result, the DNA of the 1 pg/microliter series could be detected.

According to the above described Examples and Comparative Example, it was found that chemiluminescence could be detected with high sensitivity by employing a stimulable phosphor sheet formed with a stimulable phosphor layer containing a stimulable phosphor of barium fluorobromide and uniformly irradiating it with the low energy X-rays and that chemiluminescence could be detected with high sensitivity by employing a stimulable phosphor sheet formed with a stimulable phosphor layer containing a stimulable phosphor of barium fluorobromide and adding to the chemiluminescent substance a sensitizing agent capable of shifting the wavelength of the light emitted from the chemiluminescent substance.

The present invention has thus been shown and described with reference to specific embodiments. However, it should be noted that the present invention is in no way limited to the details of the described arrangements but changes and modifications may be made without departing from the scope of the appended claims.

For example, although examples of a dot-blotting for detecting gene amount and producing reference data regarding genes and for determining the base sequence of DNA by electrophoresis are illustrated in the above described embodiments, the present invention is not limited to such chemiluminescent detecting methods and can also be applied to chemiluminescent detecting methods such as chemiluminescent detecting methods for determining the base sequence of a nucleic acid other than DNA obtained by electrophoresis, screening genes obtained by electrophoresis or colony hybridization, the separation or identification of a protein or the estimation of the molecular weight or properties of a protein. Therefore, the labeling substance and the chemiluminescent substance are not limited to those used in the embodiments and substances suitable for the respective chemiluminescent detecting methods can be used.

Further, although a stimulable phosphor of barium fluorobromide is used in the above described embodiments, the stimulable phosphor may be of any type insofar as it can store radiation energy and can be stimulated by visible light to release the radiation energy stored therein in the form of light. Therefore, not only other barium fluorohalide phosphors than the barium fluorobromide phosphor but also other alkaline earth metal fluorohalide phosphors, europium activated complex halide phosphors, cerium activated trivalent metal oxyhalide phosphors, cerium activated rare earth oxyhalide phosphors, europium activated complex halide phosphors and the like can be used in the present invention.

Moreover, although AMPPD is used as a chemiluminescent substance in the above described embodiments, other chemiluminescent substances may be used in the present invention.

Furthermore, although the sensitizing agent "RUBY" produced by and available from TROPIX, 47 Wiggins Avenue, Bedford, Mass. 01730, U.S.A. is added to the chemiluminescent substance AMPPD in the embodiment shown in FIGS. 3A and 3B and the sensitizing agent "EMERALD" produced by and available from TROPIX, 47 Wiggins Avenue, Bedford, Mass. 01730, U.S.A. is added to the chemiluminescent substance AMPPD in the embodiments shown in FIGS. 4A and 4B and 5A and 5B, as in the embodiment shown in FIG. 1A and 1B, a sensitizing agent need not necessarily be added. Further, the sensitizing agent "EMERALD" produced by TROPIX may be added instead of the sensitizing agent "RUBY" in the embodiment shown in FIGS. 3A and 3B and the sensitizing agent "RUBY" produced by TROPIX may be added instead of the sensitizing agent "EMERALD" in the embodiments shown in FIGS. 4A and 4B and 5A and 5B. Moreover, the sensitizing agent may instead be of any type other than the sensitizing agents "RUBY" and "EMERALD" produced by TROPIX insofar as it can convert the wavelength of the chemiluminescent light to a wavelength which can efficiently erase the energy of X-rays, electron beams or ultraviolet rays stored in the stimulable phosphor layer.

Figure 1B:
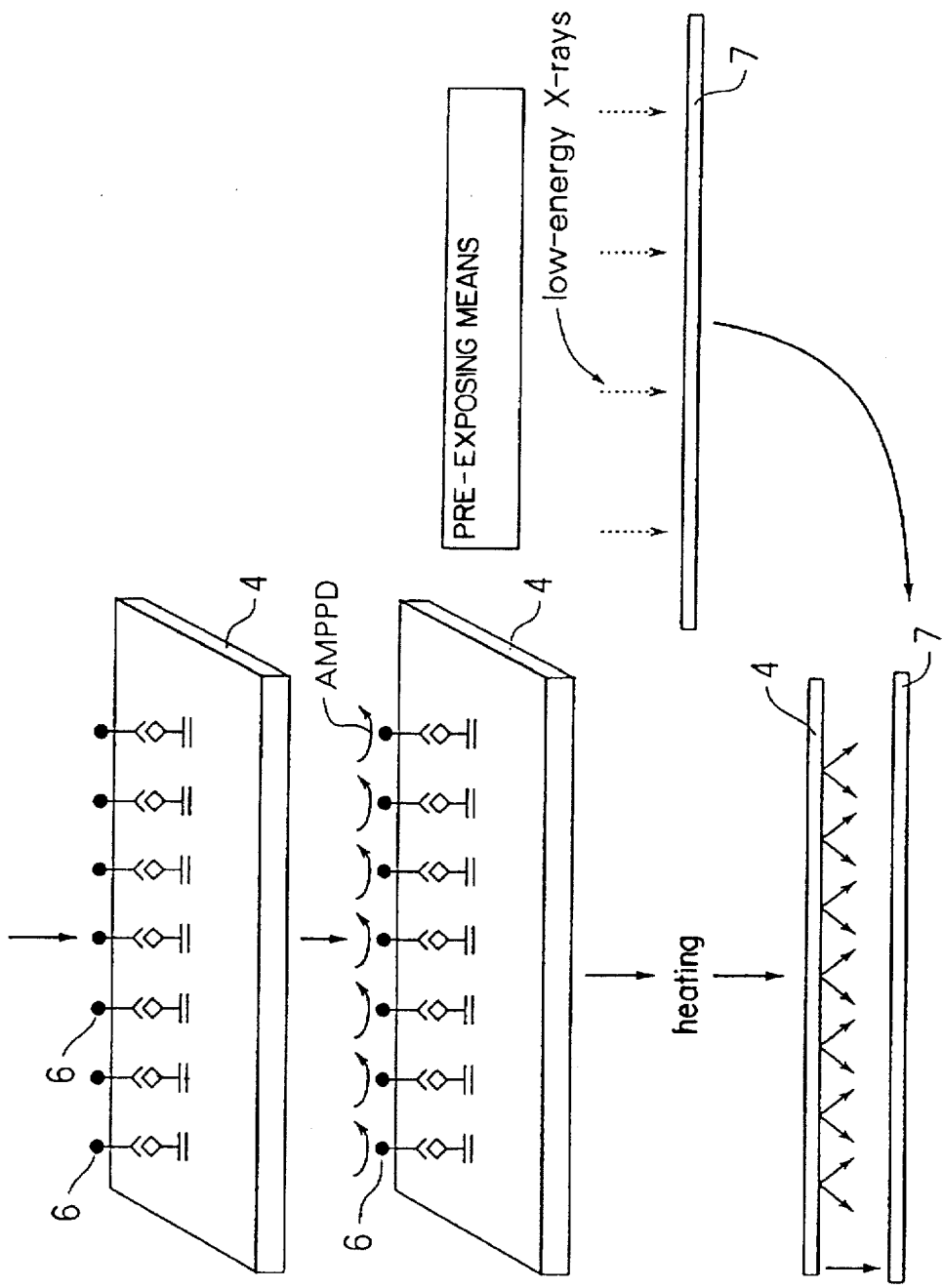
Figure 5B:
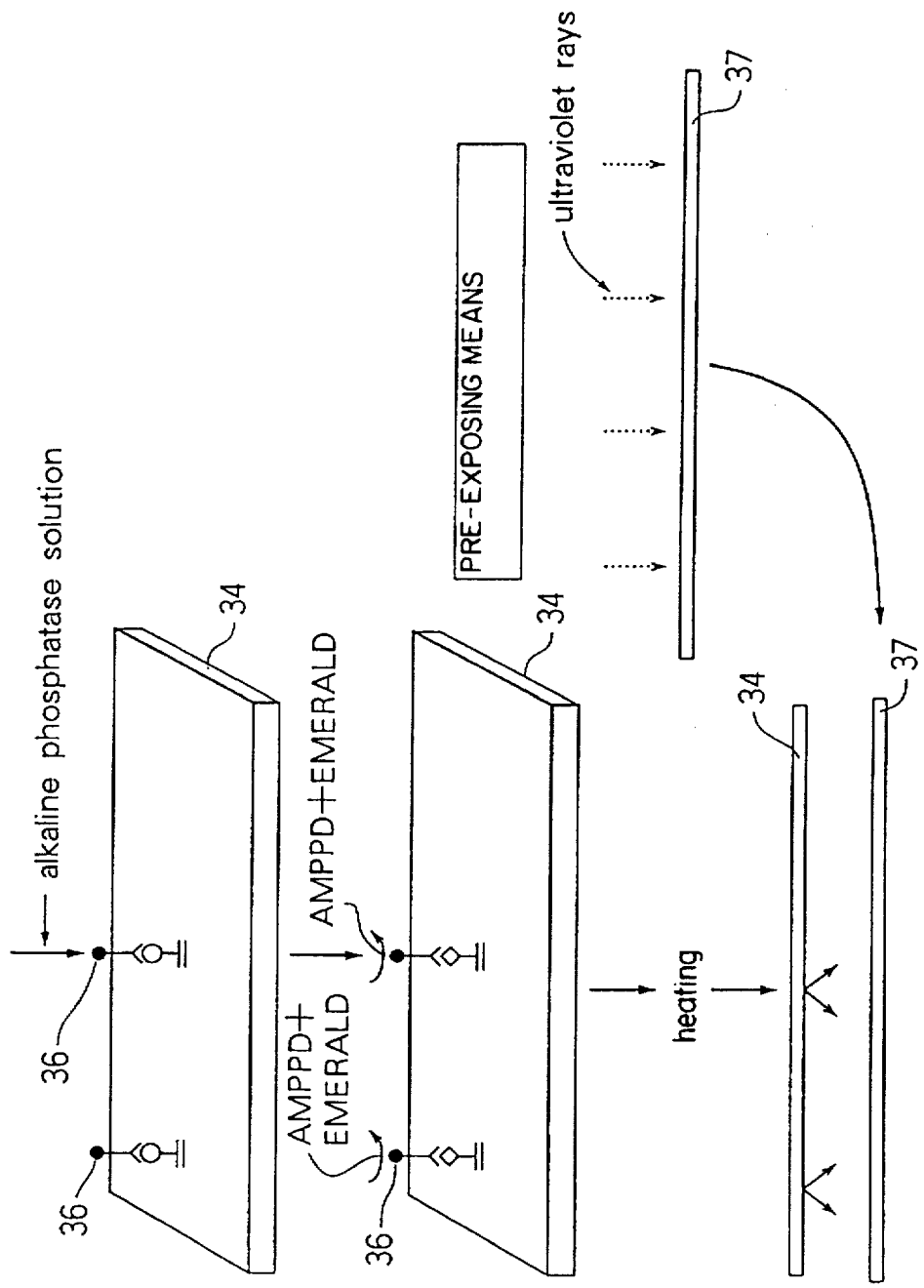

Further, the stimulable phosphor layer formed on the stimulable phosphor sheet 7, 37 is uniformly irradiated with low energy X-rays to store the energy of X-rays therein in the embodiments shown in FIGS. 1 and 3, the stimulable phosphor layer is uniformly irradiated with low energy electron beams to store the energy of electron beams therein in the embodiment shown in FIGS. 4A and 4B and the stimulable phosphor layer is uniformly irradiated with low energy ultraviolet rays to store the energy of ultraviolet rays therein in the embodiment shown in FIGS. 5A and 5B. Instead, however, it is possible to uniformly irradiate the stimulable phosphor layer with low energy electron beams or low energy ultraviolet rays to store the energy of electron beams or ultraviolet rays therein in the embodiments shown in FIGS. 1A and 1B and 3A and 3B and it is also possible to uniformly irradiate the stimulable phosphor layer with low energy X-rays to store the energy of X-rays therein in the embodiments shown in FIGS. 4A and 4B and 5A and 5B. Moreover, it is possible to uniformly irradiate the stimulable phosphor layer with other radiation having low energy to store the energy of radiation therein.

Furthermore, in the above described embodiments, although information regarding chemiluminescence converted to digital signals is displayed as images on the screen of the CRT 22, it may be displayed on other display means or be reproduced on a recording media such as a photographic film.

According to the present invention, it is possible to provide a chemiluminescent detecting method and apparatus which can effectively produce information relating to a biopolymer such as information relating to a gene with high accuracy by using a stimulable phosphor sheet which can be easily handled and used for both the chemiluminescent detecting method and the autoradiographic detecting method.

We claim:

1. A chemiluminescent detecting method comprising the following steps:

uniformly irradiating with radiation a stimulable phosphor sheet formed with a stimulable phosphor layer containing a stimulable phosphor, which can store an energy of radiation and be stimulated by visible light to emit the energy of radiation in a form of light, thereby storing energy of radiation uniformly therein;

selectively labeling a biopolymer with a labeling substance which can produce chemiluminescent light by contact between itself and a chemiluminescent substance, causing the biopolymer labeled with the labeling substance and the chemiluminescent substance to come into contact with each other;

exposing the stimulable phosphor sheet to chemiluminescent light produced by the contact of the biopolymer labeled with the labeling substance and the chemiluminescent substance for a predetermined period of time to release energy stored in the stimulable phosphor sheet relative to the position and intensity of the chemiluminescent light from the labeled biopolymer in contact with the chemiluminescent substance;

scanning the exposed stimulable phosphor sheet with an electromagnetic wave to stimulate release of the remaining stored energy; and photoelectrically converting the released remaining stored energy into an image representative of the chemiluminescent light released by the labeled biopolymer.

2. A chemiluminescent detecting method in accordance with claim 1 wherein the chemiluminescent substance contains a sensitizing agent which can change the wavelength of light emitted from the chemiluminescent substance.

3. A chemiluminescent detecting method in accordance with claim 2 wherein the stimulable phosphor is a barium fluorohalide phosphor and the sensitizing agent contains poly-[vinylbenzyl (benzyl dimethyl ammonium chloride)] shown by the following general formula as a main component

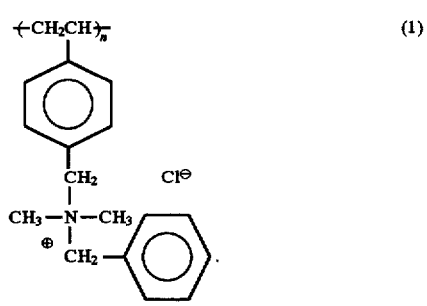

4. A chemiluminescent detecting method in accordance with claim 3 wherein the sensitizing agent contains fluorescent dye shown by the following formula (2) or (3)

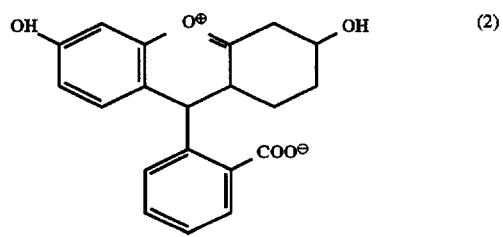

or

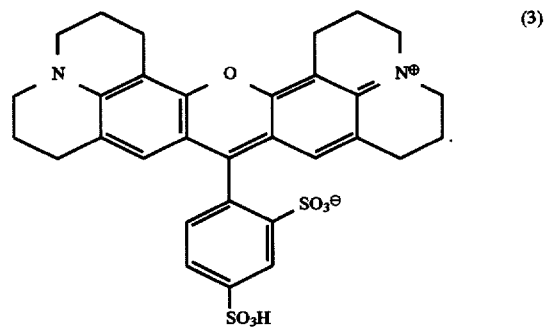

5. A chemiluminescent detecting method in accordance with claim 3 wherein the sensitizing agent contains an anionic dodecyloxy-polyoxyethylene sulfate sodium salt, $C_{12}H_{25}O(CH_2CH_2O)_nSO_3Na$.

6. A chemiluminescent detecting method in accordance with claim 3 wherein the sensitizing agent contains NaCl or inorganic cations.

7. A chemiluminescent detecting method in accordance with claim 3 wherein the sensitizing agent contains a small amount of sodium acetate.

8. A chemiluminescent detecting method in accordance with claim 2 wherein the sensitizing agent contains a very small amount of fluorescent dye and a surface active agent.

9. A chemiluminescent detecting method in accordance with claim 2 wherein the radiation includes X-rays, α-rays, β-rays, γ-rays and electron beams.

10. A chemiluminescent detecting method in accordance with claim 9 wherein X-rays having an energy equal to or less than 20 KV are selected as the radiation.

11. A chemiluminescent detecting method in accordance with claim 9 wherein electron beams having an energy equal to or less than 100 KV are selected as the radiation.

12. A chemiluminescent detecting method in accordance with claim 2 wherein the sensitizing agent contains a very small amount of fluorescent dye.

13. A chemiluminescent detecting method in accordance with claim 2 wherein the sensitizing agent contains a small amount of a surface active agent.

14. A chemiluminescent detecting method in accordance with claim 2 wherein the sensitizing agent contains a small amount of inorganic substance.

15. A chemiluminescent detecting apparatus for detecting chemiluminescent light produced by contact between a labeled biopolymer selectively labeled with a labeling substance and a chemiluminescent substance, said apparatus comprising:

pre-exposing means for uniformly irradiating with radiation a stimulable phosphor sheet formed with a stimulable phosphor layer containing a stimulable phosphor, which can store energy of radiation and be stimulated by visible light to emit the energy of radiation in a form of light, thereby obtaining a pre-exposed stimulable phosphor sheet which stores energy of radiation uniformly therein;

irradiating means for irradiating with stimulating light the stimulable phosphor sheet after it has released energy of radiation stored therein in the form of light owing to the exposure of the stimulable phosphor to the chemiluminescent light;

scanning means for scanning the exposed stimulable phosphor sheet with an electromagnetic wave to stimulate release of the remaining stored energy; and converting means for photoelectrically converting the released remaining stored energy into an image representative of the chemiluminescent light released by the labeled biopolymer.

* * * * *